United States Patent
Rudko et al.

(10) Patent No.: US 7,204,255 B2
(45) Date of Patent: Apr. 17, 2007

(54) ENDOVASCULAR TISSUE REMOVAL DEVICE

(75) Inventors: Robert I Rudko, Holliston, MA (US); Mark R. Tauscher, Medfield, MA (US); Richard P. Yeomans, Jr., Medway, MA (US)

(73) Assignee: PLC Medical Systems, Inc., Franklin, MA (US)

( * ) Notice: Subject to any disclaimer, the term of this patent is extended or adjusted under 35 U.S.C. 154(b) by 0 days.

(21) Appl. No.: 10/628,794

(22) Filed: Jul. 28, 2003

(65) Prior Publication Data

US 2005/0027337 A1 Feb. 3, 2005

(51) Int. Cl.
*A61B 19/00* (2006.01)

(52) U.S. Cl. ............................ 128/898; 606/15
(58) Field of Classification Search .............. 606/2, 606/10, 13–19, 27–52, 200; 607/88–89, 607/101; 128/898
See application file for complete search history.

(56) References Cited

U.S. PATENT DOCUMENTS

| | | | |
|---|---|---|---|
| 467,852 A | 1/1892 | Buckelew | |
| 1,858,544 A | 5/1932 | Erickson | |
| 2,267,110 A | 12/1941 | Kinley et al. | |
| 3,271,869 A | 9/1966 | Ratner | |
| 3,533,166 A | 10/1970 | Pino, Jr. | |
| 3,772,794 A | 11/1973 | Hopler, Jr. | |
| 4,213,246 A | 7/1980 | Stevens | |
| 4,411,648 A | 10/1983 | Davis et al. | |
| 4,587,975 A | 5/1986 | Salo et al. | |
| 5,074,871 A | 12/1991 | Groshong | |
| 5,176,693 A | 1/1993 | Pannek, Jr. | |
| 5,275,169 A | 1/1994 | Afromowitz | |
| 5,356,382 A | 10/1994 | Picha et al. | |
| 5,366,490 A * | 11/1994 | Edwards et al. ............... 607/99 |
| 5,370,685 A | 12/1994 | Stevens | |
| 5,411,552 A | 5/1995 | Andersen et al. | |
| 5,428,903 A | 7/1995 | Pocci | |
| 5,545,214 A | 8/1996 | Stevens | |
| 5,554,185 A | 9/1996 | Block et al. | |
| 5,840,081 A | 11/1998 | Andersen et al. | |
| 5,885,244 A | 3/1999 | Leone et al. | |
| 6,010,511 A | 1/2000 | Murphy | |
| 6,033,359 A | 3/2000 | Doi | |
| 6,081,737 A | 6/2000 | Shah | |
| 6,106,515 A | 8/2000 | Winston et al. | |
| 6,110,200 A | 8/2000 | Hinnenkamp | |
| 6,168,614 B1 | 1/2001 | Andersen et al. | |
| 6,287,321 B1 | 9/2001 | Jang | |
| 6,423,055 B1 | 7/2002 | Farr et al. | |

(Continued)

OTHER PUBLICATIONS

Boudjemline et al., "Steps Toward Percutaneous Aortic Valve Replacement", 2002 http://www.circulationaha.org, American Heart Association, Inc., pp. 775-778 (Feb. 12, 2002).

(Continued)

*Primary Examiner*—Michael Peffley
(74) *Attorney, Agent, or Firm*—Iandiorio & Teska

(57) ABSTRACT

An endovascular tissue removal device including a lumen with a distal steerable tip portion extending from a joint portion, registration means for holding the joint portion fixed in place in the vasculature, and a source of ablation energy in communication with the lumen whereby tissue can be resected by ablation energy as the tip portion is steered within the vasculature.

3 Claims, 4 Drawing Sheets

U.S. PATENT DOCUMENTS

| | | |
|---|---|---|
| 6,425,916 B1 | 7/2002 | Garrison et al. |
| 6,450,976 B2 | 9/2002 | Korotko et al. |
| 6,485,485 B1 | 11/2002 | Winston et al. |
| 6,517,515 B1 | 2/2003 | Eidenschink |
| 6,560,889 B1 | 5/2003 | Lechen |
| 2002/0045848 A1* | 4/2002 | Jaafar et al. ............. 604/20 |
| 2002/0058995 A1 | 5/2002 | Stevens |
| 2002/0095116 A1 | 7/2002 | Strecter |

OTHER PUBLICATIONS

Cardima, *Naviport® Deflectable Tip Guiding Catheter*, Brochure, Cardima, Inc. (Oct. 2001).

U.S. Appl. No. 10/600,175, filed Jun. 20, 2003, Rudko et al.

U.S. Appl. No. 10/753,693, filed Jan. 7, 2004, Rudko et al.

U.S. Appl. No. 10/447,532, filed May 29, 2003, Rudko et al.

* cited by examiner

ENDOVASCULAR TISSUE REMOVAL DEVICE

FIELD OF THE INVENTION

This invention relates to endovascular aortic valve replacement.

BACKGROUND OF THE INVENTION

Currently, replacement of a malfunctioning heart valve is accomplished by a major open-heart surgical procedure requiring general anesthesia, full cardio-pulmonary bypass with complete cessation of cardio-pulmonary activity, and a long period of hospitalization and recuperation. In most cases, the native valve is resected (cut-out) and the replacement valve then installed.

As an alternative to open heart surgery, those skilled in the art have attempted to devise systems for endovascular heart valve replacement to overcome the disadvantages associated with open-heart surgery. U.S. Pat. No. 5,370,685, for example, discloses a procedure device capsule connected to a tube and delivered to the site via a guide wire introduced in the femoral artery of a patient. The device capsule houses an expandable barrier attached to balloon segments. Once the guide wire is removed and the barrier is expanded, a tissue cutting blade assembly is advanced in the tube and rotated by a DC motor to resect the existing valve. The barrier traps any debris cut by the tissue cutting blade assembly. Tissue is then suctioned out via the tube. Next, the cutting blade assembly is removed, the barrier balloons are deflated, and the barrier is brought back into the capsule and the capsule itself is removed.

Then, a valve introducer capsule is advanced to the site. The capsule houses a replacement valve and includes a pusher disk and inflatable balloon segments. After the balloon segments are inflated, the pusher disk pushes the replacement valve into position and a mounting balloon is used to expand the replacement valve and to secure it in place. Then, the introducer capsule is removed. The '685 patent is hereby incorporated herein. See also U.S. Pat. Nos. 5,545,214; 6,168,614; 5,840,081; 5,411,552; 5,370,685; and published Patent Application No. U.S. 2002/0058995 A1. These patents are also incorporated herein.

The problem with such a system is that the tissue cutting blade assembly is less than optimal and does not provide very precise cutting especially given the fact that the valve is made of both soft and hard tissue because it is heavily calcified or contains fibrotic tissue. Thus, the blades may buckle or bind as they alternately contact soft and hard tissue.

It is also presumed that pressure must be exerted on the blades. Control of this pressure and the control of the rotation rate, however, is not disclosed in the '685 patent. There is no margin for error in the resection procedure. If too much tissue is cut in certain areas, for example, the aorta can be permanently damaged. Moreover, the existing valve typically fails because of calcification of the valve resulting in stenosis or insufficiency. Using cutting blades for valve resection and an improper orientation or improper pressure on the cutting blades or the wrong rate of rotation can result in too little or too much tissue removal and/or imprecise cutting and/or blade buckling or binding as the blades alternately contact soft and hard (calcified) tissue.

Other relevant art includes the following, also included herein by this reference. Published Patent Application No. U.S. 2002/0095116 A1 discloses an aortic filter, an artery filter, and a check valve attached to the distal end of a canula for resecting an aortic valve from within the aorta. The mechanism for resecting the aortic valve, however, is not disclosed. U.S. Pat. No. 6,287,321 also discloses a percutaneous filtration catheter. U.S. Pat. No. 5,554,185 discloses an inflatable prosthetic cardiovascular valve but does not disclose any specific method of resecting the existing or native valve.

U.S. Pat. No. 6,425,916 discloses a percutaneous approach with a valve displacer for displacing and holding the native valve leaflets open while a replacement valve is expanded inside the native valve. In this way, the native valve does not need to be resected. In many cases, however, such a procedure can not be carried out due to the poor condition of the native valve. And, because the native valve occupies space, the largest aperture possible by the replacement valve may not provide sufficient blood flow.

U.S. Pat. Nos. 6,106,515 and 6,485,485, also incorporated here by this reference, disclose various expandable laser catheter designs.

SUMMARY OF THE INVENTION

It is therefore an object of this invention to provide a more precise tissue cutting apparatus for endovascular heart valve replacement.

It is a further object of this invention to provide such a tissue cutter which is more effective than prior art blade type tissue cutters.

It is a further object of this invention to provide a tissue cutter which provides effective resection even if the valve is heavily calcified or has fibrotic tissue.

It is a further object of this invention to provide such a tissue cutter which does not require a high rate of rotation.

It is a further object of this invention to provide such a tissue cutter which eliminates the need for precise pressure control.

The invention results from the realization that a more effective and more precise tissue cutting apparatus for endovascular heart valve replacement is effected by the use of an optical fiber inside a deflectable tip catheter and an expandable balloon which registers the assembly inside the heart for resection by laser ablation as the deflectable tip steers the distal end of the optical fiber.

This invention features an endovascular tissue removal device comprising a lumen including a distal steerable tip portion extending from a joint portion, registration means for holding the joint portion fixed in place in the vasculature, and a source of ablation energy in communication with the lumen whereby tissue can be resected by ablation energy as the tip portion is steered within the vasculature.

In the preferred embodiment, the registration means includes an inflatable balloon about the joint portion, the source of ablation energy is a laser, the distal steerable tip portion includes a deflectable tip catheter, and there is an optical fiber inside the deflectable tip catheter and connected to the laser. The device may further include an expandable barrier for trapping any debris resected. The device, in one embodiment, includes an expandable mechanism inflatable on the ventricular side of the valve for supporting the leaflets of the valve. An absorptive surface on the expandable mechanism absorbs ablation energy. Typically, the expandable mechanism is a balloon.

An endovascular tissue removal device in accordance with this invention features a lumen including a distal steerable tip portion extending from a joint portion, an inflatable balloon about the joint portion for registering the joint portion fixed in place in vasculature, and a source of ablation energy in communication with the lumen whereby tissue can be resected by ablation energy as the tip portion is steered within the vasculature.

A lumen includes a distal steerable tip portion extending from a joint portion, registration means holds the joint portion fixed in place in vasculature, and an optical fiber is disposed within the lumen and steerable by the distal steerable tip portion and connected to a source of ablation energy to resect tissue as the tip portion is steered within the vasculature.

In the preferred embodiment, the endovascular heart removal device of this invention includes a catheter including a deflectable tip, a laser source, an optical fiber within the catheter connected to the laser source, and an inflatable balloon for registering the deflectable tip in vasculature to resect a heart valve with laser energy as the deflectable tip portion is used to steer the distal end of the optical fiber within vasculature.

A method of resecting a valve, the method in accordance with this invention includes endovascularly introducing a lumen with a distal steerable tip portion to a position proximate a valve to be resected; registering the lumen in place in the vasculature; directing ablation energy through the lumen; and steering the distal steerable tip portion to resect the valve. In one example, an expandable mechanism is positioned on the ventricular side of the valve and inflated to support the leaflets of the valve during resection.

BRIEF DESCRIPTION OF THE DRAWINGS

Other objects, features and advantages will occur to those skilled in the art from the following description of a preferred embodiment and the accompanying drawings, in which.

DISCLOSURE OF THE PREFERRED EMBODIMENT

Figure 1:
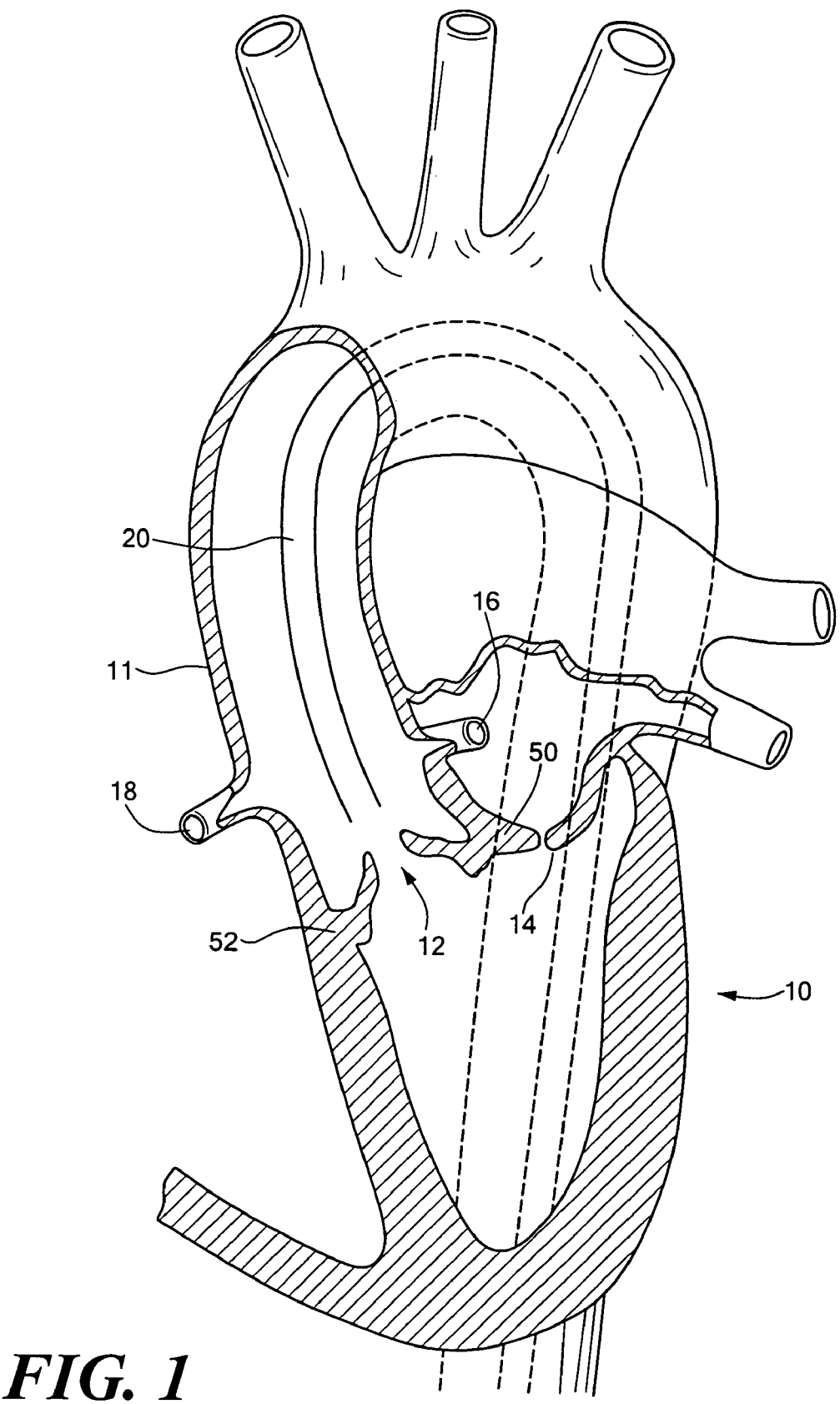
FIG. 1 is a schematic view showing a typical human heart.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings.

FIG. 1 schematically shows heart 10 with aorta 11, aortic valve 12, mitral valve 14, and coronary arteries 16 and 18. The idea behind percutaneous valve replacement surgery is to deliver a catheter 20 proximate valve 12 to resect it and to secure a replacement prosthetic valve in place. Resecting the native valve, however, is problematic. Those skilled in the art have devised inflatable barriers such as barrier 30, FIG. 2 used to trap tissue during resection. See also U.S. Pat. No. 6,287,321 and Published Patent Application No. U.S. 2002/0095116 A1. Barrier 30 traps any tissue cut during valve resection.

Figure 3:
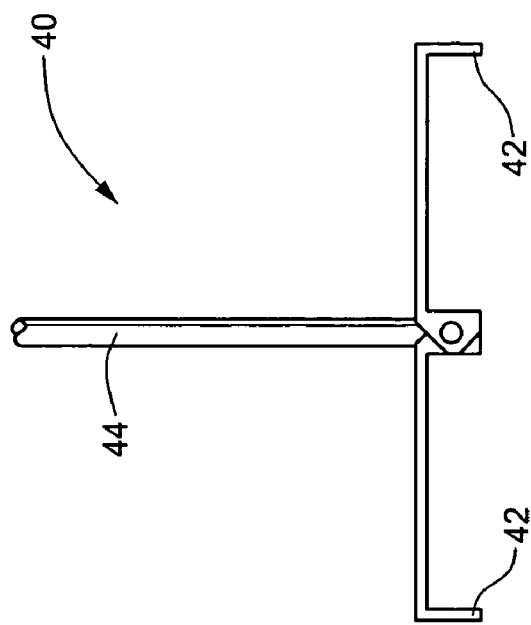
FIG. 3 is a schematic view showing a prior art tissue cutter used in endovascular aortic valve replacement procedures.

But, the prior art teaches resection of the native valve tissue by tissue cutter 40, FIG. 3 with blades 42. Tissue cutter 40 is connected to shaft 44 rotated by a DC motor presumably at a very high rate of rotation in order to effect tissue cutting. It is also presumed that pressure must be exerted on the blades. Control of this pressure and the control of the rotation rate, however, is not disclosed in the '685 or '321 patents.

As shown in FIG. 1, there is no margin for error in the resection procedure. If too much tissue is cut in areas 50 or 52, for example, the aorta can be permanently damaged. Moreover, existing valve 12 (or 14) typically fails because of calcification of the valve resulting in stenosis or insufficiency. Using cutting blades for valve resection and an improper orientation or improper pressure on the cutting blades or the wrong rate of rotation can result in too little or too much tissue removal and/or imprecise cutting and/or blade buckling or binding as the blades alternately contact soft and hard (calcified) tissue.

The problem is so profound that some skilled in the art have attempted to eliminate native valve resection and instead theorize that a prosthetic valve can be expanded directly within native valve 12 (or 14) using a valve displacer to hold the native valve open. As delineated above, however, due to the condition of the native valve, such a procedure is not always possible or effective.

Figure 4:
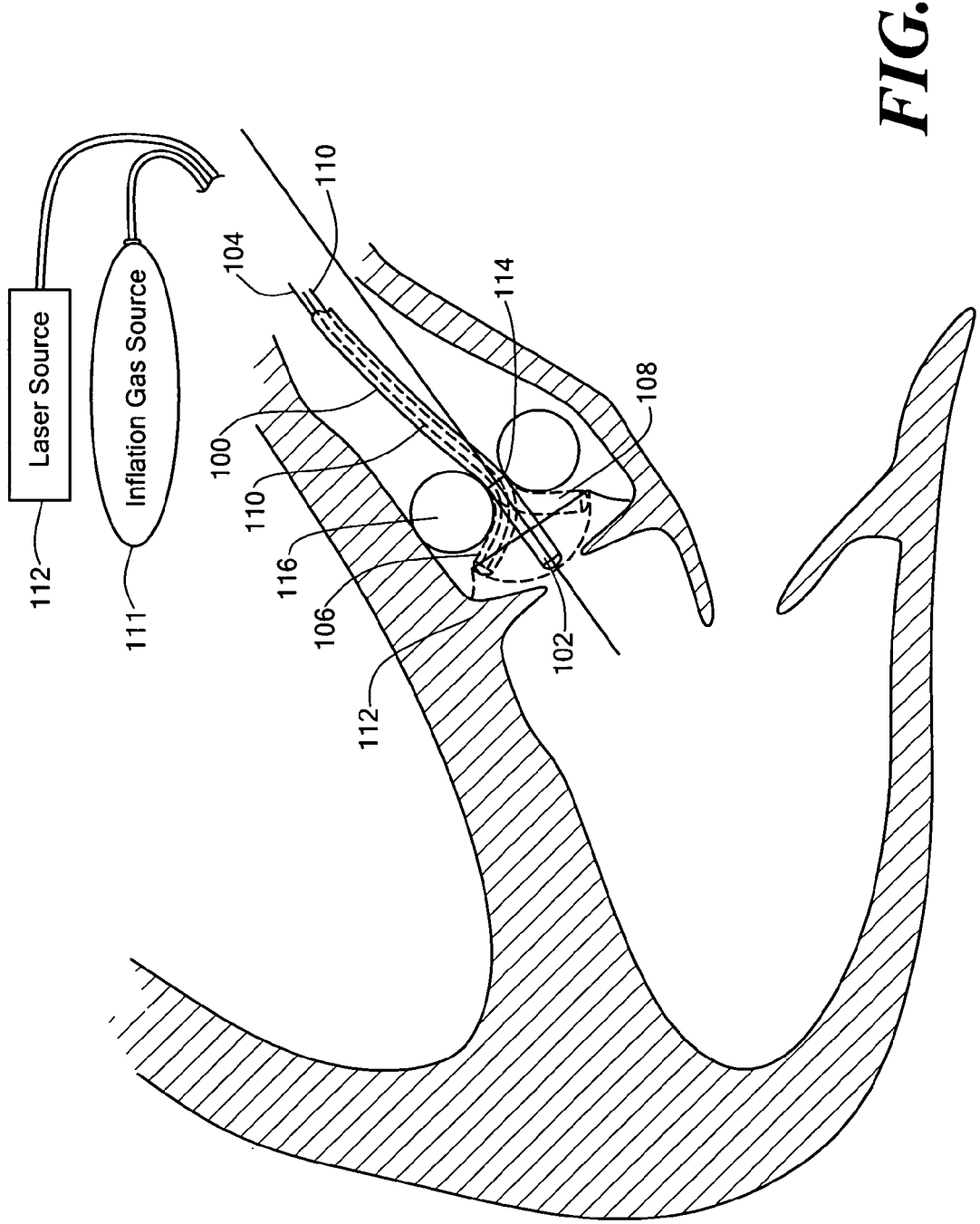
FIG. 4 is a schematic three-dimensional view showing the primary components associated with the endovascular tissue removal device of the subject invention.

In the subject invention, more precise tissue cutting is effected even if native valve 12, FIG. 4 is heavily calcified or has fibrotic tissue. The preferred endovascular tissue removal device of this invention includes lumen 100 advanceable within the patient's vascular with distal steerable tip portion 102, typically a deflectable tip catheter which employs wire 104 to maneuver tip portion as shown in phantom at 106 and 108. One such deflectable tip catheter is sold by Cardima of Freemont, Calif. under the trademark Naviport®. Optical fiber 110 is disposed in catheter 100. The distal end of optical fiber 110 extends to, nearly to, or slightly beyond the distal end of catheter 100. In the preferred embodiment, optical fiber 110 is connected to laser source 112. Other sources of ablation energy, however, may be used. The subject invention also features registration means for holding joint portion 114 of lumen 100 fixed in place in the vasculature for precise steering of distal steerable portion 102 to resect valve 12 with laser energy. In the preferred embodiment, the registration means includes inflatable balloon 116 about joint portion 114 inflated with insufflation gas from source 111.

Figure 2:
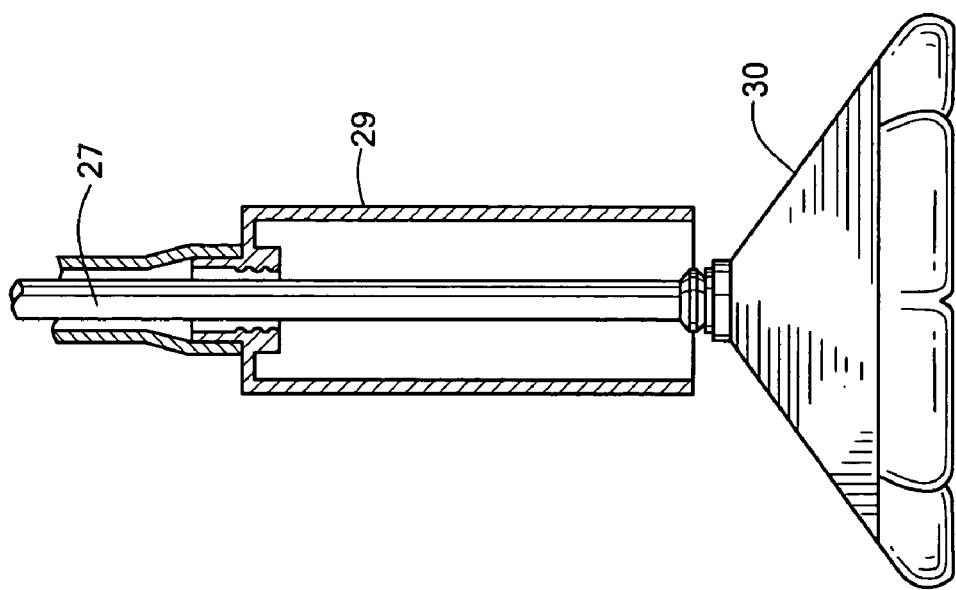
FIG. 2 is a schematic view of a prior art inflatable barrier used in endovascular aortic valve replacement procedures.

A complete system would include an expandable barrier such as barrier 30, FIG. 2 to trap tissue during resection. In one example, the subject invention is used as follows. Device capsule 29, FIG. 2 is delivered to the site and barrier 30 expanded. Lumen 100, FIG. 4 is then delivered within tube 127 and balloon 116 inflated. The physician then manipulates wire 104 to steer tip portion 102 as shown at 106 and 108 to resect valve 12 using laser energy from source 112. After full resection, balloon 116 is deflated and lumen 100 removed. The tissue is then sucked out of tube 27 and barrier 30 is brought back into capsule 29 which is then withdrawn. Finally, a valve introducer is advanced to the site and the replacement valve installed.

In this way, the problems associated with prior art blade type tissue cutters are eliminated and tissue cutting is far more precise by the use of optical fiber 110 within deflectable tip catheter 100 and expandable balloon 116 which registers the assembly inside the heart for resection by laser ablation as the deflectable tip portion steers the distal end of optical fiber 110.

Figure 5:
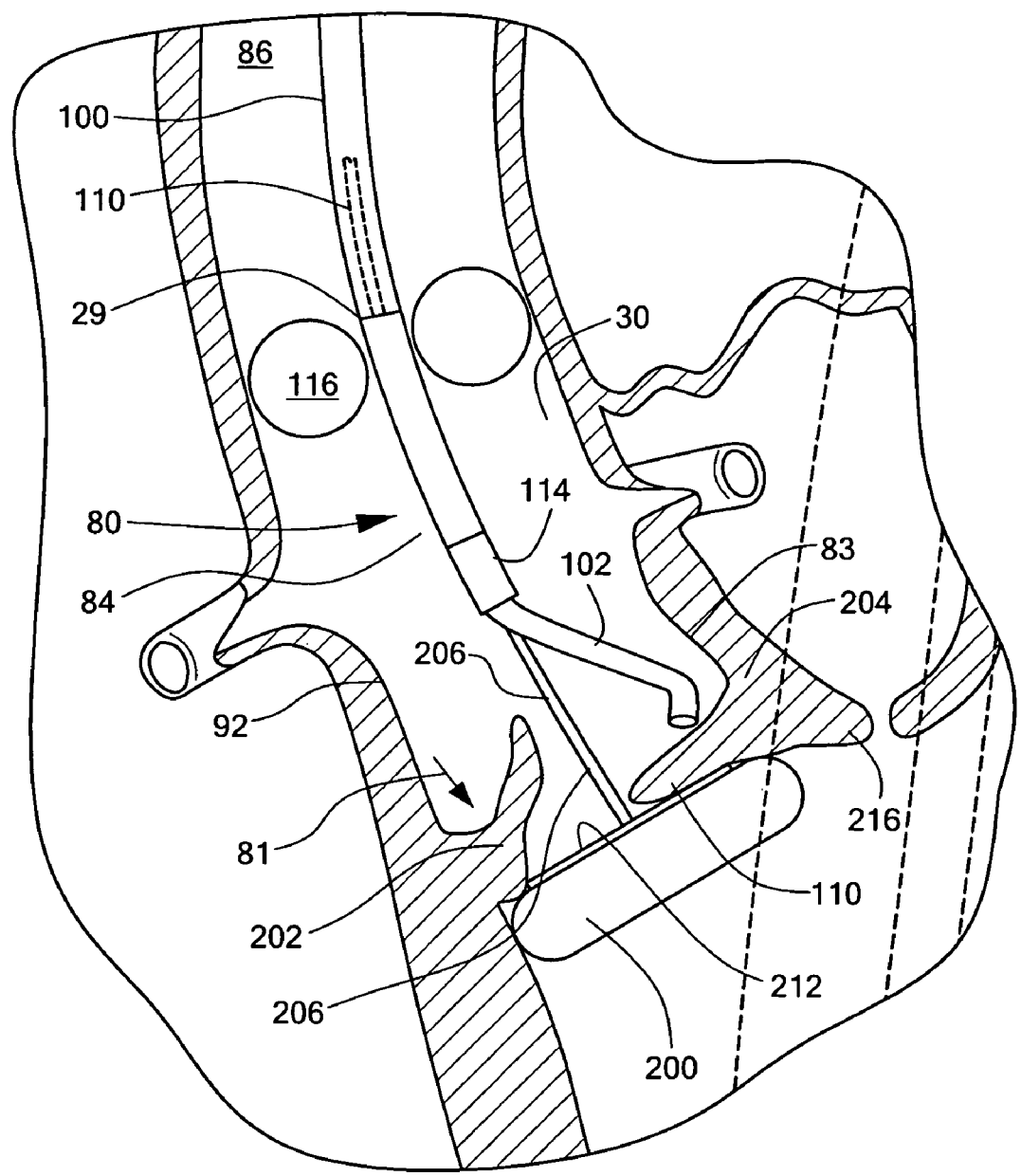
FIG. 5 is a schematic three-dimensional view showing another embodiment of the tissue removal device of the subject invention.

A more complete system is shown in FIG. 5 including tissue removal device 102 and lower balloon 200 disposable on the ventricular side of the heart valve under leaflets 202 and 204. Balloon 200 is connected to inflation conduit 206 which extends within multi-lumen catheter 100. An outer suction conduit may include a port for withdrawing tissue. Balloon 200 performs several important functions. First, it supports leaflets 202 and 204 of the valve as they are pushed closed by tissue removal device 102 as shown in FIG. 5 before cutting for more accurate cutting. Balloon 200 with laser energy absorption layer 212 also prevents inadvertent cutting of any portion of mitral valve 216.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims:

What is claimed is:

1. A method of resecting a valve, the method comprising:
    endovascularly introducing a lumen with a distal steerable tip portion to a position proximate a valve to be resected;
    registering the lumen in place in the vasculature;
    directing ablation energy through the lumen; and
    steering the distal steerable tip portion to resect the valve.

2. The method of claim 1 further including the step of endovascularly introducing an expandable mechanism on the ventricular side of the valve and inflating the expandable mechanism to support the leaflets of the valve during resection.

3. A method of resecting a valve, the method comprising:
    endovascularly introducing a lumen with a distal steerable tip portion to a position proximate a valve to be resected;
    registering the lumen in place in the vasculature;
    endovascularly introducing an expandable mechanism on the ventricular side of the valve and inflating the expandable mechanism to support the leaflets of the valve during resection;
    directing ablation energy through the lumen; and
    steering the distal steerable tip portion to resect the valve.

* * * * *